United States Patent

Prescott et al.

(10) Patent No.: US 6,962,086 B2
(45) Date of Patent: Nov. 8, 2005

(54) RHEOMETER

(75) Inventors: Philip Prescott, Glouchestershire (GB); Nick Ourrossoff, Gloucester (GB)

(73) Assignee: Prescott Instruments Limited, Gloucestershire (GB)

( * ) Notice: Subject to any disclaimer, the term of this patent is extended or adjusted under 35 U.S.C. 154(b) by 41 days.

(21) Appl. No.: 10/399,667

(22) PCT Filed: Nov. 12, 2001

(86) PCT No.: PCT/GB01/04993

§ 371 (c)(1),
(2), (4) Date: Apr. 21, 2003

(87) PCT Pub. No.: WO02/42739

PCT Pub. Date: May 30, 2002

(65) Prior Publication Data

US 2003/0183016 A1 Oct. 2, 2003

(30) Foreign Application Priority Data

Nov. 22, 2000 (GB) .............................. 0028441

(51) Int. Cl.[7] .............................................. G01N 3/24
(52) U.S. Cl. ....................................................... 73/846
(58) Field of Search .......................... 73/846, 856, 859, 73/860

(56) References Cited

U.S. PATENT DOCUMENTS

| 2,752,778 A | | 7/1956 | Edward et al. | |
|---|---|---|---|---|
| 3,500,677 A | * | 3/1970 | Broyles et al. | 73/54.37 |
| 3,706,221 A | * | 12/1972 | Fletcher et al. | 73/54.37 |
| 4,343,190 A | * | 8/1982 | Danko et al. | 73/846 |
| 4,552,025 A | * | 11/1985 | Barker et al. | 73/846 |
| 5,063,785 A | * | 11/1991 | Labuz et al. | 73/821 |
| 5,631,409 A | * | 5/1997 | Rajagopal et al. | 73/54.35 |

FOREIGN PATENT DOCUMENTS

| DE | 36 36 872 | 5/1988 |
|---|---|---|
| EP | 0 136 994 A2 | 4/1985 |
| EP | 0 285 453 | 10/1988 |
| GB | 2 173 599 A | 10/1986 |
| GB | 2 259 676 | 3/1993 |

* cited by examiner

*Primary Examiner*—Max Noori
(74) *Attorney, Agent, or Firm*—Young & Thompson

(57) ABSTRACT

A rheometer 1, an example of which is shown in FIG. 1, comprising an upper die 2 and a lower die 3. Extending on the vertical axis of this die arrangement is a pneumatic cylinder shaft 6, which is connected to the heater element 4 and insulator layer 5 of the upper die 2. The lower die 3 is supported by a bearing 8 which allows a lower die to rotate about an axis which is in line with that of the pneumatic cylinder 6. A lower die 3 is caused to oscillate in a rotation manner of at a vertical axis in line with the pneumatic cylinder, which is also connected to a transducer 12 which measures the force needed to keep the upper die to substantially stationary as rotation occurs. Alternatively, a lower die 2 can be have substantially stationery while a rotor head 16 holds the material to be tested. This case the forces required to maintain oscillation of the rotor head 16 in the material are tested by the transducer 12.

13 Claims, 4 Drawing Sheets

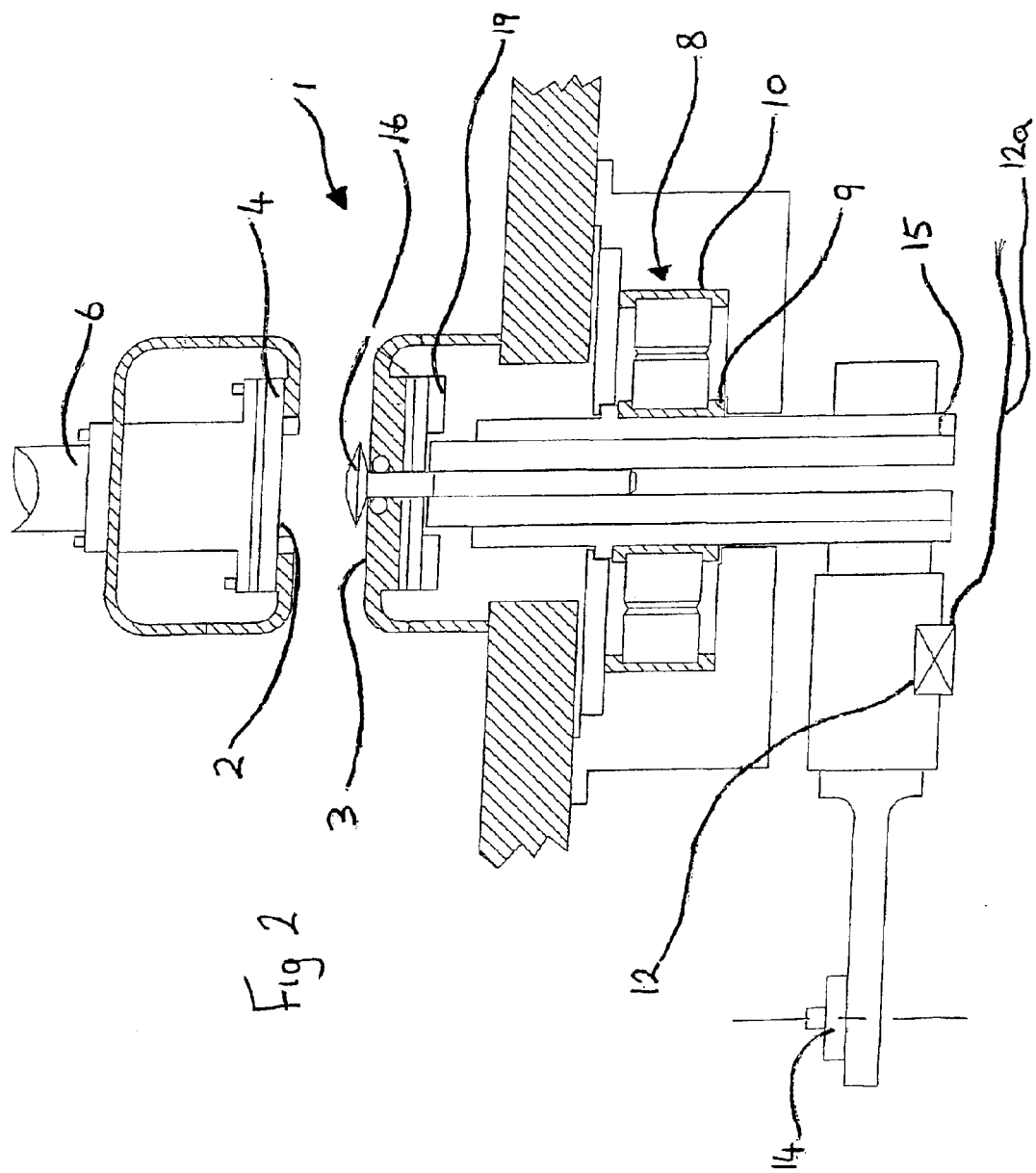

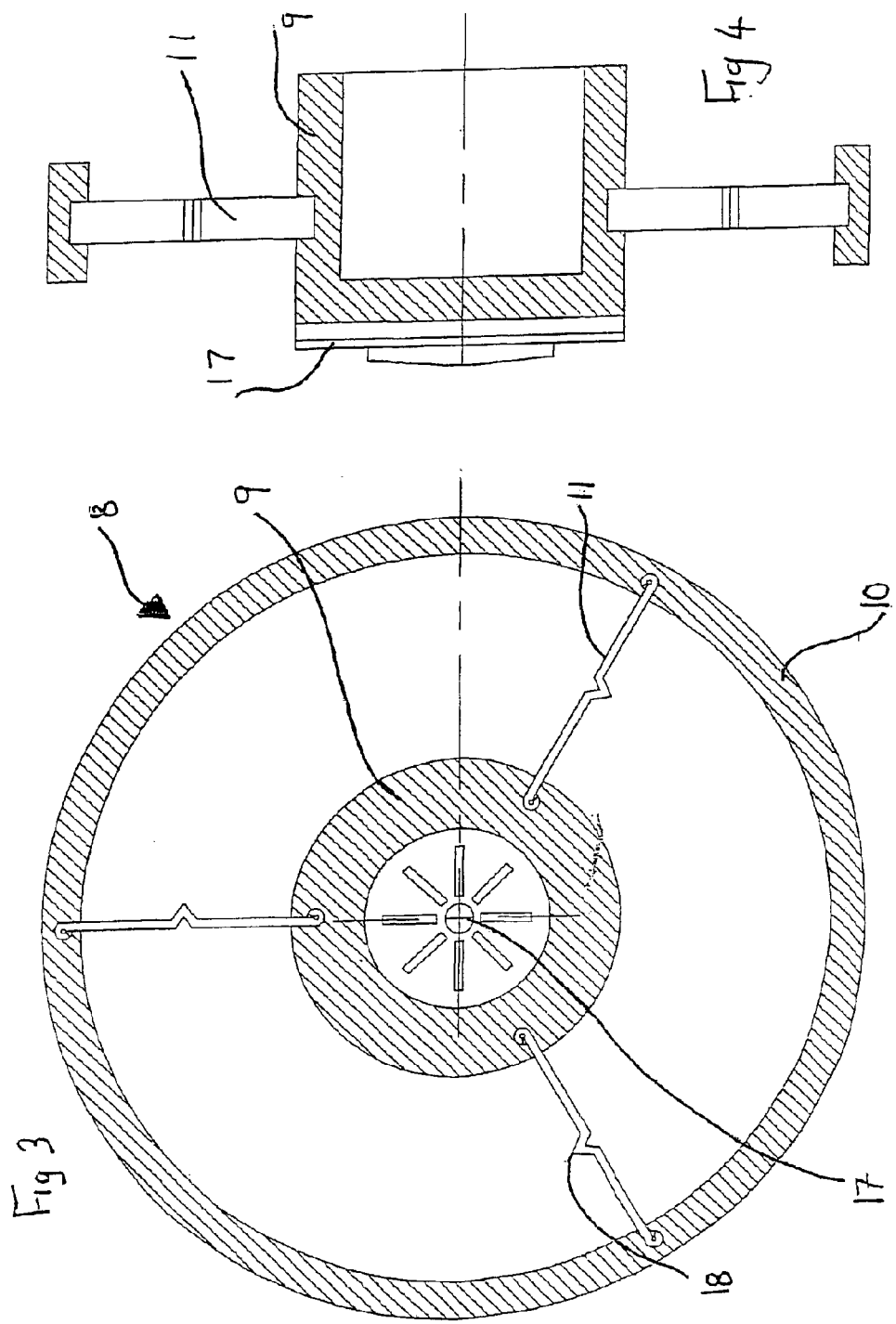

RHEOMETER

Figure 1:
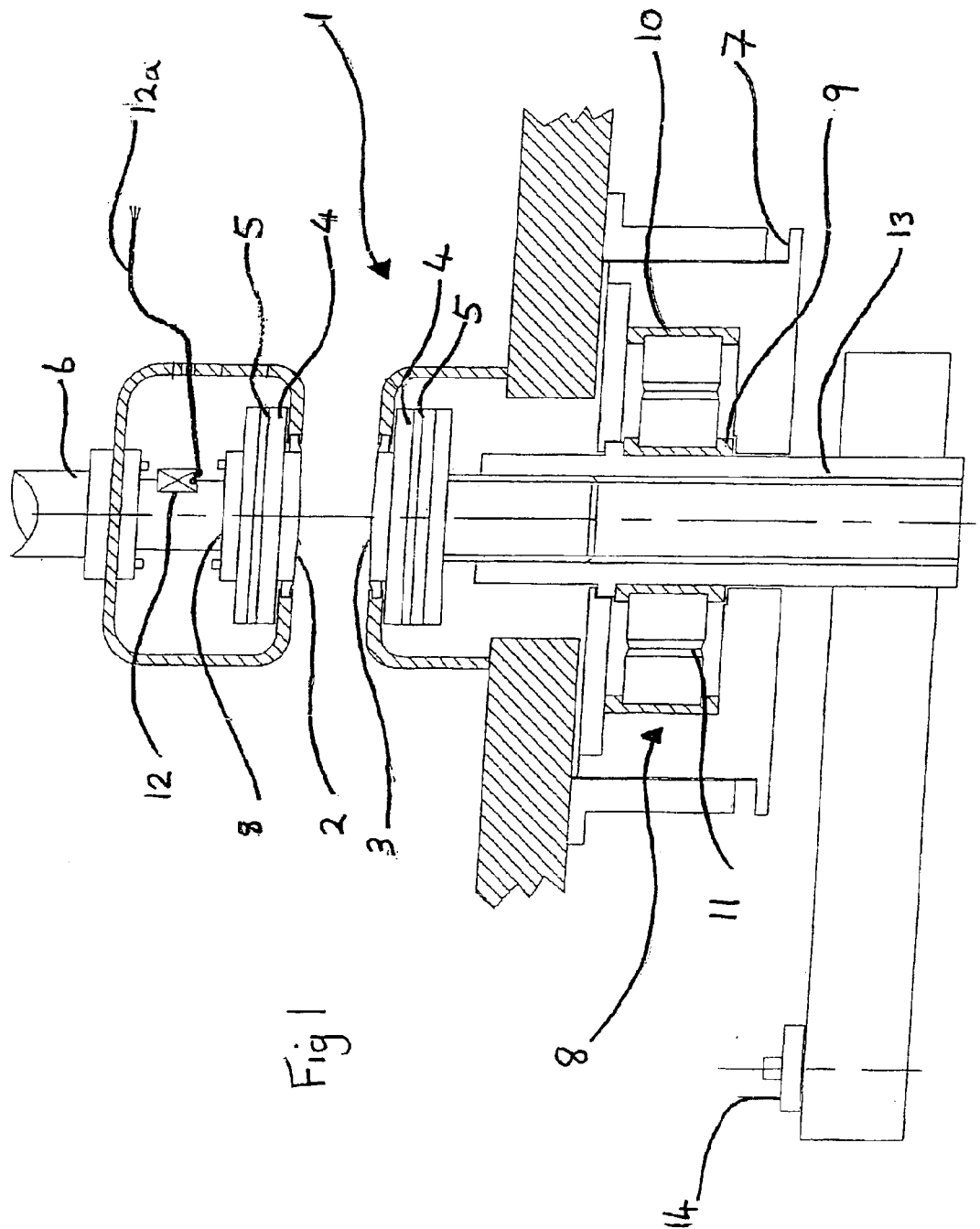

This invention relates to apparatus for testing the physical properties of a material and, in particular but not exclusively, to a rheometer, having a bearing, which allows for more accurate measurements during testing.

Rheometers are used in a wide variety of chemical and material processing industries, including paint and pigment manufacture, paper manufacture, catalysts, ceramics and in rubber production. Raw materials are mixed or processed to a given formulation and then tested using a rheometer, to measure the viscoelastic properties of the material before the production stage is carried out. In the rubber industry, rheometers are used to judge the curing characteristics of individual batches of rubber and are used in the production of tyres, seals and gaskets.

The response of the materials to the mechanical forces, such as dynamic shear, induced by the rheometer is an important factor in the selection of batches of materials to be used in manufacture. Measurements taken using the rheometer are used to check that any batch meets the required specification.

Known rheometers include those as described in EP 545728, where a sample is placed between opposed circular plates. The two plates are then brought into contact with the sample, and kept under pressure while the plates are heated. One plate is oscillated angularly relative to the other opposed plate, at given frequencies and amplitudes, which are selected according to the tests being carried out and the material that is being tested. The angular displacement of the one plate relative to the other is measured precisely using an optical decoder. The rheological properties of the material are then calculated by a computer, using the measured torque and angular displacement of the plates.

The lower plate may be supported by a bearing such as a ball and race bearing, or alternatively an air bearing, which allows the plate to oscillate but remain steady under an axial load.

A problem associated with known rheometers is that there is an exacerbation of bearing wear. This wear is due to the bearing absorbing heat from the lower plate, and the fact that the bearing is only operating at an oscillation of a small number of degrees, for example 1 or 2 degrees. Because the bearing is being operated at a combination of high temperature, high axial load, together with a small oscillatory motion this leads to bearing wear and consequently, early bearing failure. Even more importantly there is deterioration of test accuracy. There is the added problem that when a bearing fails, the rheometer cannot be used until the bearing is replaced and this can slow down production, resulting in increased manufacturing costs for a product.

A first aspect of the invention consists in an apparatus for testing the physical properties of a sample, including a pair of spaced relatively moveable plates for receiving the sample between them and for applying a force to the sample on relative movement of said plates, and a bearing for mounting one of the plates for relative movement thereof, characterised in that the bearing includes a support member whereby flexure of the support member allows the relative movement.

In preference, the bearing comprises first and second bearing parts connected by the support member, the bearing parts being moveable relative to one another on movement of the plate, due to flexure of said support member.

Preferably, the first bearing part comprises a substantially vertical member connected to at least one plate, with the second bearing part comprising a member coaxial with the first bearing part. It envisaged that the plates may be in a vertical arrangement with there being an upper and a lower plate. The bearing usually supports the lower plate, but it is envisaged that the bearing may be connected to the upper plate. Further, an arrangement is envisaged where the plates are in a substantially horizontal face to face arrangement, with the bearing being associated with one or other of the plates.

It is particularly preferred that the first bearing part comprises a substantially vertical cylindrical member with the second bearing part being formed of a cylinder coaxial with the first bearing part. However, it is envisaged that an arrangement may be where the first bearing part comprises a vertical member which moves axially, relative to the second bearing part.

Ideally, the first and second bearing parts are connected by support members extending radially from the first bearing part. Each support member may comprise an arm or rib extending from the first bearing part. Another arrangement is where the support member is in the form of a blade extending along the length of the first bearing part.

In preference, there are three support members but the number of can be increased or decreased, depending on the parameters that are to be measured for a material.

It is advantageous that the support members include at least one crimp along their length to allow for increased flexing when the first and second bearing parts move relative to one another.

An advantageous arrangement of the support members is that they radiate from the vertical member forming the first bearing part. This may be as a result of positioning within a holding groove in the first bearing part or alternatively, the member may be, for example, spot welded to the first bearing part. It is also envisaged that the support member may be releasably connected to the first and second bearing parts.

A preferred material for the bearing parts is one that can withstand high pressure and temperature. Such materials include sprung steel but it is possible to use other metals or composites, or even polymer materials, which have high pressures and temperature tolerances.

In a second aspect of the invention there is provided a method of testing the physical properties of a material, wherein a sample is loaded between two plates, a first of the plates being held in a substantially stationary position while a second plate which is supported by a bearing comprising first and second bearing parts connected by a support member is moved relative to the other plate, wherein the movement of the first and second bearing parts is as a result of flexure of said support member, with the force required to maintain the first plate in said substantaially stationary position being measured by a transducer which is in connection with a computer for collating measurements from the transducer.

Preferably, the first bearing part is rotated relative to the second bearing part. However, it is possible for the first and second bearing parts to be moved in an axial plane relative to one another.

The apparatus tests, typically, small samples of material, which are usually about 4 $cm^3$ in volume. The plates are closed around the material to be tested at a pressure of approximately 10 kilo Newtons (dN) per meter and are heated to up to 250° C. During a test the plates are oscillated in relation to one another at 1.67 Hz, although these can vary from 0.01 Hz to 100 Hz and at an amplitude of 0.5°, although this can vary from 0.05 to 15 degrees. The shear force of a sample moving against the surface of one plate, caused by the movement of a second plate is an important factor in measuring the characteristics of a material being tested by a rheometer. The reaction force of a plate due to movement of a sample or indeed another plate, can be measured by a transducer and force readings are taken over a period of time during the test and plotted out in real time to produce a curve characteristic of the material under test.

The term plates also includes dies, whether profiled or not and the specific description will refer to dies.

Although the invention has been defined above, it is to be understood that it includes any inventive combination of the features set out above or in the following specific description.

Figure 5:
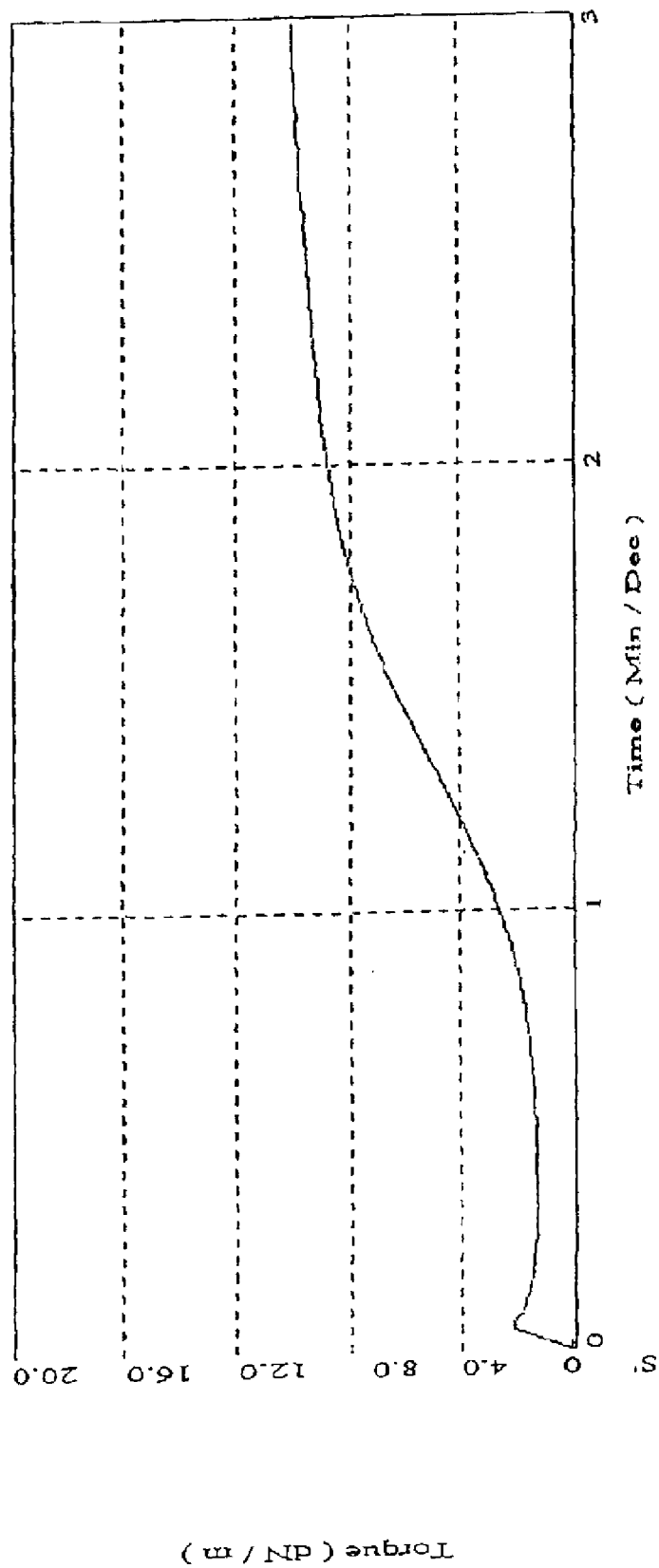

For a better understanding of the invention, an embodiment will now be described, by way of example, with reference to the accompanying drawings, in which:

FIG. 1: shows a side view of a rheometer according to the invention;

FIG. 2: shows a side view of another rheometer according to the present invention;

FIG. 3: shows a view from above of a support for a die to be used with a rheometer according to the present invention;

FIG. 4: shows a side view of a bearing for a die according to the present invention;

FIG. 5: shows a graph of the test results produced using a rheometer according to the present invention.

FIG. 1 shows a rheometer 1, comprising an upper die 2 and a lower die 3. Each die is connected to respective heater element 4. The heater elements are each in turn, in contact with an insulation layer 5, which reduces heat loss from the respective dies in order to provide more accurate testing conditions. Extending along the vertical axis of the die arrangement is a pneumatic cylinder shaft 6, which is connected to the heater element 4 and insulator layer 5 of the upper die 2. This cylinder shaft 6 is used to move the upper die away from the lower die when loading a test material and then towards said lower die 3 when the material is being tested. The pneumatic cylinder shaft 6, is also connected to a transducer 12, which in turn is connected to a cable 12a leading to a computer. The upper die is held in a substantially stationary by pneumatic cylinder 6.

The lower die 3 is supported by a bearing 8 which allows the lower die to rotate about an axis which is in line with that of the pneumatic cylinder 6.

As shown in more detail in FIG. 3 the bearing 8 comprises a first bearing part, which is a substantially vertical shaft 9 connected to an outer cylinder 10 by support members 11. The support members 11 extend radially from the vertical shaft 9. The central shaft 9, is connected to the die 3 by a spindle 17. The support members 11 each have a crimp 18 along their length. Although a single crimp is shown, there may be a series of crimps or it may be possible for some members to have no crimp regions.

It will be noted that the illustrated bearing includes no rubbing movements and so it much less subject to wear. It is also less susceptible to deterioration resulting from heat and pressure as the support members are large enough to accommodate both.

The transducer 12 measures the force needed to keep the upper die 2 substantially stationary as the lower die 3 is caused to oscillation in a rotational manner about a vertical axis in line with the pneumatic cylinder. Preferably, an oscillation of 1.67 Hz is used at an amplitude of 0.5°. The transducer 12 provides readings, during the course of the test, which are fed to a computer and plotted out in real time to produce a curve for the material under test. Typically, the transducer produces 12 readings per cycle but this can vary from 4 to 2000 readings per cycle.

The lower die 3 is housed by a threaded bearing housing 7, which can adjust the gap between the dies 2,3.

The lower die 3 is connected by a support shaft 13, which again is in the axial plane of the pneumatic shaft 6 is connected by a link arm 14 which in turn is driven by a motor. The motor causes the support shaft 13 to rotate which in turn causes rotation of the lower die 3, during sample testing.

During testing, the material placed between the dies, goes through a series of stages from the plastic to the semi-liquid, to the cross-linking stage and finally to a maximum plateau where a measurement is taken.

The samples produce a list of results along a sine wave and a Fourier analysis is made of the elastomer modulus and viscous modulus, which is reproduced in graph form. Alternatively, rather than Fourier analysis, the results may be used to calculate simple arithmetic progression to give a torque value for each cycle of the sine wave motion. The graph provides a range of tolerances within the test material should fall for it to be acceptable to be used in a production process. A curve of the plottings taken is illustrated in FIG. 5. In this case the sample is held at a temperature of 175° C. (within +/− 5° C.) and the test is carried out over a 3 minute period. There are a number of test point gates within which the wave characteristic of the sample must fall for the sample to be acceptable for its specified use.

FIG. 2 shows a similar rheometer arrangement to that of FIG. 1. In this case both the upper die 2 and the lower die 3 are held in a substantially stationary position around the sample that is placed between them. The lower die is supported by frame 19. In this case there is a main shaft 15, within the support shaft 13, for the lower die 3. The main shaft 15 extends through the shaft 13 and terminates with a rotor head 16, extending into the space between the two dies 2,3. The rotor head will actually extend into the body of the material being tested and the torque that is being produced as a result of the movement of head 16 within the material will be the measurement that are taken. The torque will be transmitted to the bearing 8. Transducer 12, which is associated with the lower die will take measurements from the bearing 8. In this case the measurements taken are the force, or forces required to maintain oscillation of the rotor head 16 in the material. These measurements are plotted against time, to measure the characteristics of the material between the die and again a graph is plotted in a similar fashion to the graph shown in FIG. 5.

It is to be understood that the above detailed description is an embodiment of the invention and is provided by way of example only. Various details of design and construction may be modified without departing from the true spirit and scope of the invention as set out in the appended claims.

What is claimed is:

1. Apparatus for testing the physical properties of a sample, including a pair of spaced relatively rotationally moveable plates for receiving the sample between them and for applying a force to the sample on relative rotational movement of said plates, and a bearing for mounting one of the plates for relative rotational movement thereof, characterised in that the bearing includes a support member whereby flexure of the support member allows the relative rotational movement.

2. Apparatus according to claim 1, wherein the bearing comprises first and second bearing parts connected by the support member, the bearing parts being moveable relative to one another on movement of the plate, due to flexure of said support member.

3. Apparatus according to claim 2, wherein the first bearing part comprises a substantially vertical member supporting at least one plate, with the second bearing part comprising a member coaxial with the first bearing part.

4. Apparatus according to claim 2, wherein the first bearing part comprises a substantially vertical cylindrical member with the second bearing part being formed of a cylinder coaxial with the first bearing part.

5. Apparatus according to claim 2, wherein the first and second bearing parts are connected by support members extending radially from the first bearing part.

6. Apparatus according to claim 5, wherein each support member comprises an arm, rib or blade extending from the first bearing part.

7. Apparatus according to claim 5 wherein there are three support members.

8. Apparatus according to claim 5 wherein each of the support members includes at least one crimp along its length.

9. Apparatus according to claim 5, wherein the support members are an extension of the first bearing part.

10. Apparatus according to claim 2, wherein the bearing parts and the support member is sprung steel.

11. A method of testing the physical properties of a material, wherein a sample is loaded between two plates, a first of the plates being held in a substantially stationary position while a second plate which is supported by a bearing comprising first and second bearing parts connected by a support member is rotated relative to the other plate, wherein the movement of the first and second bearing parts is as a result of flexure of said support member, with the force required to maintain the first plate in said substantaially stationary position being measured by a transducer which is in connection with a computer for collating measurements from the transducer.

12. A method according to claim 11, wherein the first bearing part is rotated relative to the second bearing part.

13. A method according to claim 11, wherein the first and second bearing parts to be moved in an axial plane relative to one another.

* * * * *